Figure 1:
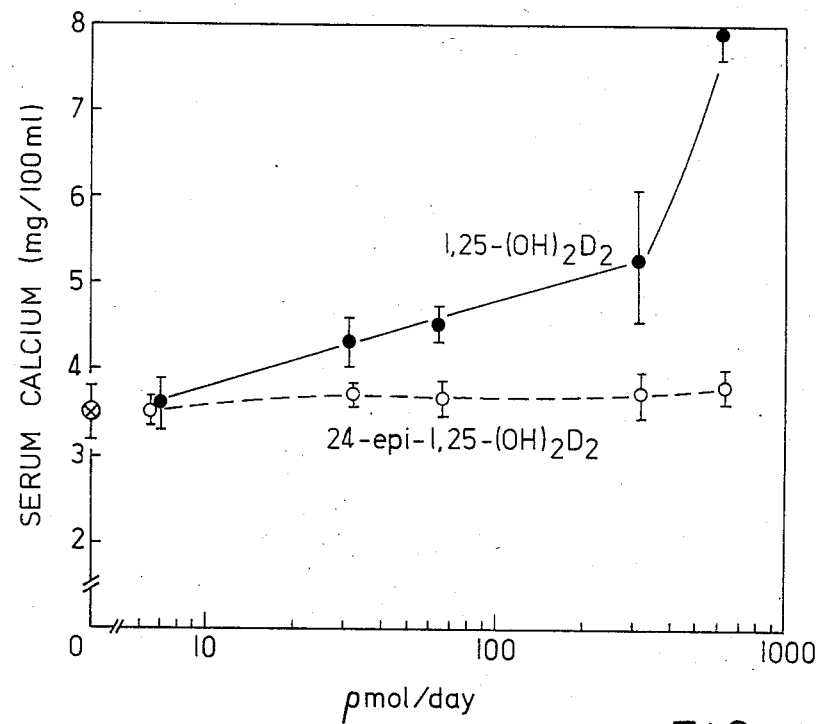

United States Patent [19]

DeLuca et al.

[11] Patent Number: 4,588,716

[45] Date of Patent: May 13, 1986

[54] METHOD FOR TREATING METABOLIC BONE DISEASE IN MAMMALS

[75] Inventors: Hector F. DeLuca; Heinrich K. Schnoes, both of Madison, Wis.

[73] Assignee: Wisconsin Alumni Research Foundation, Madison, Wis.

[21] Appl. No.: 691,824

[22] Filed: Jan. 16, 1985

Related U.S. Application Data

[63] Continuation-in-part of Ser. No. 607,327, May 4, 1984, abandoned.

[51] Int. Cl.$^4$ ............... A61K 31/595; A61K 31/59; A61K 31/56
[52] U.S. Cl. ...................... 514/168; 514/167; 514/169; 514/170
[58] Field of Search ............... 514/168, 169, 170, 171, 514/167

[56] References Cited

U.S. PATENT DOCUMENTS

| | | | |
|---|---|---|---|
| 3,697,559 | 10/1972 | DeLuca et al. | 260/397.2 |
| 3,741,996 | 6/1973 | DeLuca et al. | 260/397.2 |
| 4,159,326 | 6/1979 | Barton et al. | 424/236 |
| 4,225,596 | 9/1980 | DeLuca | 424/236 |
| 4,448,721 | 5/1984 | DeLuca et al. | 260/239.5 |

*Primary Examiner*—Douglas W. Robinson
*Attorney, Agent, or Firm*—Howard W. Bremer

[57] ABSTRACT

A method for treating or preventing metabolic bone disease characterized by loss of bone mass in mammals by administering 24-epi-1α,25-dihydroxy vitamin D$_2$ alone or in combinations thereof with bone mobilization-inducing vitamin D derivatives to said mammals.

18 Claims, 4 Drawing Figures

METHOD FOR TREATING METABOLIC BONE DISEASE IN MAMMALS

This invention was made with Government support under NIH Grant No. AM 32701 awarded by the Department of Health and Human Services. The Government has certain rights in this invention.

This application is a continuation-in-part of U.S. application Ser. No. 607,327, filed May 4, 1984 now abandoned.

TECHNICAL FIELD

This invention relates to a method for treating metabolic bone disorders characterized by loss of bone mass.

More specifically, this invention relates to a method for treating or for preventing the depletion of calcium from the bones of women entering menopause or who are postmenopausal.

Still more specifically, this invention relates to a method for treating or preventing various known forms of osteoporosis, e.g. postmenopausal, senile and steroid-induced osteoporosis, or other disease states one of the characterics of which is the loss of bone mass.

It is well know that females at the time of menopause suffer a marked loss of bone mass giving rise ultimately to osteopenia, which in turn gives rise to spontaneous crush fractures of the vertebrae and fractures of the long bones. This disease is generally known as postmenopausal osteoporosis and presents a major medical problem, both in the United States and most other countries where the life-span of females reaches ages of at least 60 and 70 years. Generally the disease which is often accompanied by bone pain and decreased physical activity, is diagnosed by one or two vertebral crush fractures with X-ray evidence of diminished bone mass. It is known that this disease is accompanied by diminished ability to absorb calcium, decreased levels of sex hormones, especially estrogen and androgen, and a negative calcium balance.

Methods for treating the disease have varied considerably but to date no really satisfactory treatment is yet known. For example, calcium supplementation by itself has not been successful in preventing or curing the disease and the injection of sex hormones, especially estrogen, which has been reported to be effective in preventing the rapid loss of bone mass experienced in postmenopausal women, has been complicated by the fear of its possible carcinogenicity. Other treatments, for which variable results have again been reported, have included a combination of vitamin D in large doses, calcium and fluoride. The primary problem with this approach is that fluoride induces structurally unsound bone, called woven bone, and in addition, produces a number of side effects such as increased incidence of fractures and gastrointestinal reaction to the large amounts of fluoride administered.

Similar symptoms characterize involutional osteoporosis, senile osteoporosis and steroid-induced osteoporosis, the latter being a recognizied result of long term glucocorticoid (cortico-steroid) therapy for certain disease states.

U.S. Pat. No. 4,225,596 suggests the use of various metabolites of vitamin $D_3$ for increasing calcium absorption and retention within the body of mammals displaying evidence of or having a physiological tendency toward loss of bone mass. The metabolites specifically named in that patent, i.e., $1\alpha$-hydroxyvitamin $D_3$, $1\alpha$-hydroxyvitamin $D_2$, $1\alpha,25$-dihydroxyvitamin $D_3$, $1\alpha,25$-dihydroxyvitamin $D_2$ and $1,24,25$-trihydroxyvitamin $D_3$, although capable of the activity described and claimed in that patent, are also characterized by the complementary vitamin D-like characteristic of mobilizing the calcium from bone in response to physiological needs. U.S. Pat. Nos. 3,833,622 and 3,901,928 respectively suggest using the hydrate of 25-hydroxyvitamin $D_3$ and $1\alpha$-hydroxyvitamin $D_3$ for treatment of osteoporosis in a general expression of utility for those compounds. It is well known that both of those compounds express traditional vitamin D-like activity, including the characteristic bone mobilization.

DISCLOSURE OF THE INVENTION

It has now been found that the 24-epi-$1\alpha,25$-dihydroxy-vitamin $D_2$ (24-epi-$1,25$-$(OH)_2D_2$) expresses a pattern of biological activity which makes it eminently suitable for the prevention or treatment of physiological disorders in mammals which are characterized by the loss of bone mass. As shown by the structures below, 24-epi-$1,25$-$(OH)_2D_2$ is the 24-methyl epimer of the known vitamin $D_2$ metabolite $1,25$-$(OH)_2D_2$. In spite of this small structural change, the 24-epi compound unexpectedly exhibits distinctly different and novel biological properties.

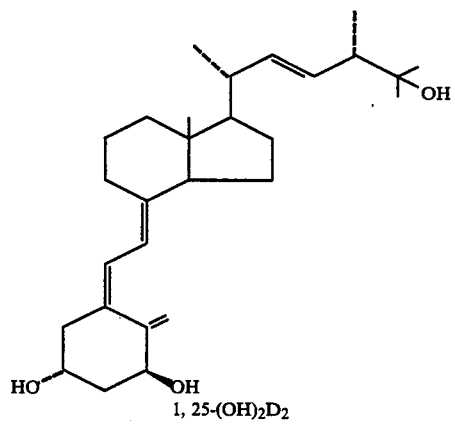

$1,25$-$(OH)_2D_2$

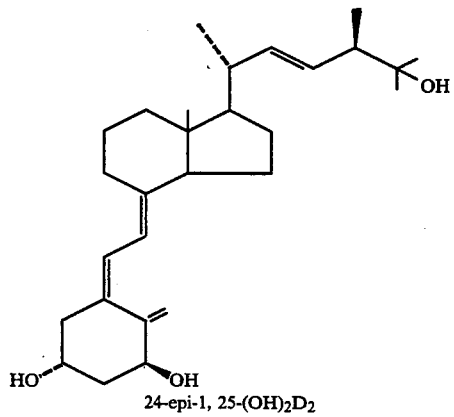

24-epi-$1,25$-$(OH)_2D_2$

Specifically, it has been found that although 24-epi-$1,25(OH)_2D_2$ expresses some of the recognized vitamin D-like characteristics affecting calcium metabolism such as increasing intestinal calcium transport, and effecting bone mineralization, it does not increase serum calcium levels of animals on a low calcium diet, even at high dosages. This observed characteristic evinces that the compound upon administration, does not mobilize bone. This combination of properties distinguishes the 24-epi compound from known vitamin D metabolites or analogs (e.g., 1,25(OH)$_2$D$_3$, 1,25-(OH)$_2$D$_2$, 1α-OH-D$_3$, and related analogs) which invariably induce both calcium absorption in intestine and mineral mobilization from bone. (See for example, U.S. Pat. No. 3,697,559, U.S. Pat. No. 3,741,996, Reeve et al, Arch. Biochem. and Biophys., Vol. 186, No. 1 (February 1978), pp. 164–167.) This lack of, or minimal bone mobilizing activity of 24-epi-1,25-(OH)H$_2$D$_2$ along with the ability of the compound to stimulate intestinal calcium absorption and to mineralize bone, indicates that it is an ideal compound for the prevention or treatment of prevalent calcium disorders which are evidenced by loss of bone mass, for example, postmenopausal osteoporosis, involutional osteoporosis, senile osteoporosis and steroid-induced osteoporosis. It will be evident that the compound will find ready application for the prevention or treatment of disease states other than those named, in which the loss of bone mass is an indication. Thus, the compound would be eminently suitable in the treatment of patients undergoing renal dialysis where loss of bone mass as a consequence of the dialysis is encountered.

The following Examples will serve to illustrate the characteristics of 24-epi-1,25-(OH)$_2$D$_2$ which contribute to its eminent suitability for the prevention or treatment of disease states that evince bone mass loss.

EXAMPLE 1

Figure 2:
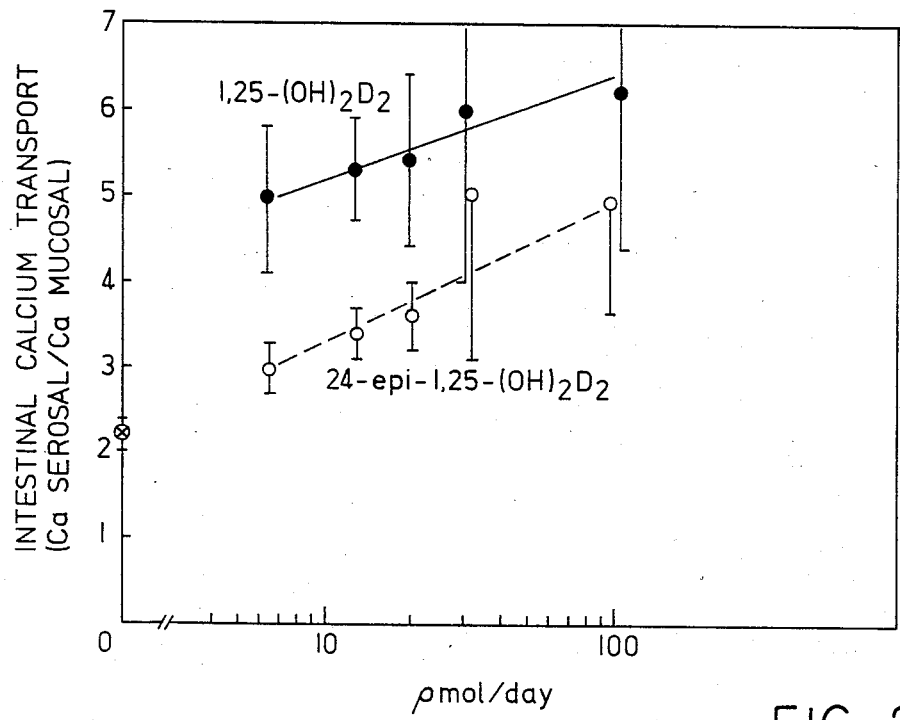

Weanling male rats were placed on the vitamin D deficient diet described by Suda et al., Journal of Nutrition 100, 1049–1052 (1970), modified to contain 0.02% calcium and 0.3% phosphorus. After two weeks on this diet, the animals were given either 1,25-dihydroxyvitamin D$_2$, or 24-epi-1,25-dihydroxyvitamin D$_2$ daily by subcutaneous injection in 0.1 ml of 5% ethanol in propanediol. Twelve hours after the last dose, the animals were killed and the blood calcium and intestinal calcium transport measured. The results of these measurements for the indicated levels of the compounds administered are shown in FIGS. 1 and 2. The intestinal calcium transport measurements shown in FIG. 2 were performed by the method of Martin and DeLuca, American Journal of Physiology 216, 1351–1359 (1969).

EXAMPLE 2

Figure 3:
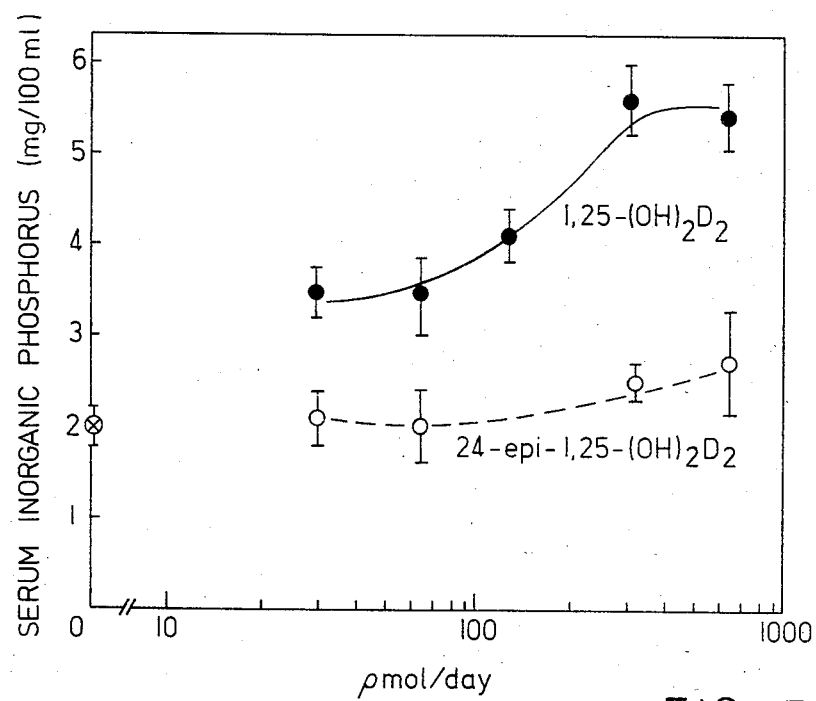

Weanling male rats were placed on a high calcium (1.2% calcium) and low phosphorus (0.1% phosphorus) diet described by Suda et al (supra). The rats were fed this diet for a period of three weeks at which time they were separated into two groups. One group was given 1,25(OH)$_2$D$_2$ while the other groups was given 24-epi-1,25(OH)$_2$D$_2$, both in 0.1 ml of 5% ethanol in propane diol subcutaneously at the dosage levels of the compounds shown by the data points in FIG. 3. These doses were continued daily for a period of seven days, at which time the animals were killed and serum inorganic phosphorus determined. Results are shown in FIG. 3.

Figure 4:
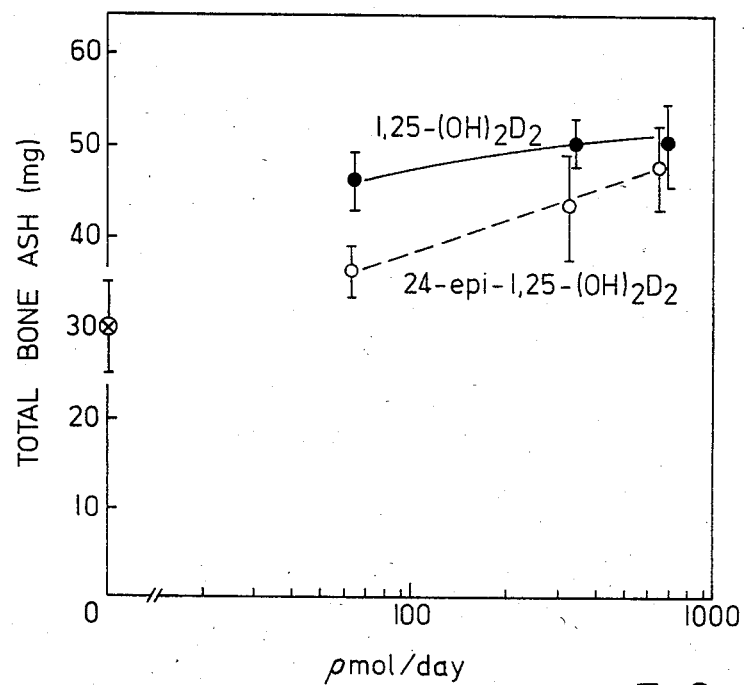

Bone ash was determined by removing the femurs from rats. The femurs were dissected free of adhering connective tissue, extracted for 24 hours in absolute ethanol, and 24 hours in diethyl ether, using a Soxhlet extractor. The bones are ashed at 600° F. for 24 hours. The ash weight was determined by weighing to constant weight. Results are shown in FIG. 4.

The results of the two studies described in Examples 1 and 2, above, illustrate that 24-epi-1,25-(OH)$_2$D$_2$ is approximately equal in potency to 1α,25-dihydroxyvitamin D$_3$ (1,25-(OH)$_2$D$_3$) in causing the mineralization of bone and in stimulating intestinal calcium transport. In short, there is no significant difference between the two groups in FIG. 2 and FIG. 4. On the other hand, the elevation of serum inorganic phosphorus which results from mobilization of bone in the case of the low phosphorus diet is very markedly affected by 1,25-(OH)$_2$D$_2$, but hardly stimulated by 24-epi-1,25(OH)$_2$D$_2$. Similarly, in the mobilization of calcium from bone, as indicated by the serum calcium levels (FIG. 1) even at the extremely high dose level of about 750 pmoles/day, the 24-epi compound had no effect, while the mobilization effect is evident at much lower doses of 1,25-dihydroxyvitamin D$_2$. Since the rise in serum calcium of rats on a low calcium diet measures the ability to mobilize bone, and since the elevation of blood phosphorus of animals on a low phosphorus diet also measures bone mobilization, these results show that 24-epi-1,25-(OH)$_2$D$_2$ provides an unexpected property, namely that it is of minimal effectiveness in mobilizing bone calcium, while being fully able to stimulate intestinal calcium transport and the mineralization of new bone, properties which make this compound highly suitable for the treatment of disease states that evince bone loss.

The unique characteristics of 24-epi-1,25-(OH)$_2$D$_2$, as set forth above, offer the additional opportunity to control the various vitamin D-responsive processes (intestinal calcium absorption, bone mineral mobilization, and bone mineralization) in a manner and to a degree heretofore not feasible. This possibility arises from the fact that the 24-epi compound of this invention may be administered to the mammal either alone (with suitable and acceptable excipients) or in combination with other vitamin D-derivatives which exhibit the full spectrum of D-like activity including the ability to promote a net bone mass gain. By such measures, it is possible therefore to combine (to whatever degree desired) the specificity of action of the 24-epi-analog with the generality of action of other vitamin D metabolites or analogs. Administration of 24-epi-1,25-(OH)$_2$D$_2$ alone will, as shown above, stimulate intestinal calcium transport and bone mineralization with no or minimal bone mineral mobilization, but the latter activity can be induced by co-administration of one or more of the known vitamin D derivatives (e.g., 1,25-(OH)$_2$D$_3$, 1α,25-(OH)$_2$D$_2$, 1α-OH-D$_3$, and related analogs). By adjusting the relative amounts of compounds administered, a degree of control over the relative magnitudes of the intestinal calcium absorption vs. bone mineral mobilization processes can be exercised in a manner not possible with the heretofore known vitamin D derivatives. Co-administration of the 24-epi compound and other vitamin D compounds with bone mobilizing activity or with other hormones which initiate the formation of new bone resorption cavities can be particularly advantageous in situation where some degree of bone mobilization is desired. For example, it is believed that in certain circumstances, bone must first be mobilized before new bone can be laid down. In such situations treatment with vitamin D or a vitamin D derivative which will induce bone mobilization, e.g. 1α-hydroxyvitamin D$_3$ or -D$_2$, 1α,25-dihydroxyvitamin D$_3$ or -D$_2$, 25-hydroxyvitamin D$_3$ or -D$_2$, 24,24-difluoro-25-hydroxyvitamin D$_3$, 24,24-difluoro-1α,25-dihydroxyvitamin D$_3$, 24-fluoro-25-hydroxyvitamin D$_3$, 24-fluoro-1α,25-dihydroxyvitamin D$_3$, 2β-fluoro-1α-hydroxyvitamin D$_3$, 2β-fluoro-25-hydroxyvitamin D$_3$, 2β-fluoro-1α,25-dihydroxyvitamin D$_3$, 26,26,26,27,27,27-hexafluoro-1α,25-dihydroxyvitamin D$_3$, 26,26,26,27,27,27-hexafluoro-25-hydroxyvitamin D$_3$, 24,25-dihydroxyvitamin D$_3$, 1α,24,25-trihydroxyvitamin D$_3$, 25,26-dihydroxyvitamin D$_3$, 1α,25,26-trihydroxyvitamin D$_3$, in combination with 24-epi-1,25(OH)$_2$D$_2$ will, by adjustment of the proportions of the 24-epi compound and the bone-mobilizing vitamin D compound in the treatment regimen permit the rate of mineralization of bone to be adjusted to achieve the desired medical and physiological ends.

24-epi-1,25-(OH)$_2$D$_2$, or combinations thereof with other vitamin D derivatives or other therapeutic agents, can be readily administered as sterile parenteral solutions by injection or intravenously, or by alimentary canal in the form of oral dosages, or trans-dermally, or by suppository. Doses of from about 0.5 micrograms to about 25 micrograms per day of 24-epi-1,25-(OH)$_2$D$_2$ per se, or in combination with other vitamin D derivatives, the proportions of each of the compounds in the combination being dependent upon the particular disease state being addressed and the degree of bone mineralization and/or bone mobilization desired, are generally effective to practice the present invention. Although the actual amount of the 24-epi-compound used is not critical, in all cases sufficient of the compound should be used to induce bone mineralization. Amounts in excess of about 25 micrograms per day of the 24-epi-compound, above, or the combination of that compound with bone mobilization-inducing vitamin D derivatives, are generally unnecessary to achieve the desired results and may not be economically sound practice. In practice the higher doses are used where therapeutic treatment of a disease state is the desired end while the lower doses are generally used for prophylactic purposes, it being understood that the specific dosage administered in any given case will be adjusted in accordance with the specific compounds being administered, the disease to be treated, the condition of the subject and the other relevant medical facts that may modify the activity of the drug or the response of the subject, as is well known by those skilled in the art.

One mode of treatment utilizing the 24-epi compound and other vitamin D compounds in combination would appear to offer particular advantages in achieving the desired goal in individual patients, depending upon the individual's condition and needs, of achieving a balance of bone mobilization and bone mineralization with a view toward a net increase in bone mineralization.

As pointed out above, it is believed that in certain circumstances bone must first be mobilized before new bone can be laid down. This process, which is known as bone remodeling and is an important aspect of bone health is thoroughly described by H. M. Frost in "Bone Dynamics in Osteoporosis and Osteomalacia," Henry Ford Hospital Surgical Monograph Series, Charles A. Thomas Co., Springfield, 1966. The remodeling involves resorption of damaged bone by an osteoclastic-medicated process. Thus, immediately following resorption of old bone, bone-forming cells, known as osteoblasts are laid down. The osteoblasts then form new bone that becomes mineralized and is strong healthy bone as compared to the bone which has been resorbed. It is accepted that the remodeling process plays an important role in maintaining not only bone health but the appropriate shape of the bone.

It is also accepted that an important factor involved in initiating bone resorption sites is the circulating hormonal form of vitamin D, i.e. either 1,25-dihydroxyvitamin D$_3$ or 1,25-dihydroxyvitamin D$_2$ or other hormones, for example, parathyroid hormone, which are characterized by that ability. Thus, the administration of any hormone which will initiate the formation of new bone resorption cavities which are then subsequently filled in to form new bone, is an important first step in the bone remodeling process. Since continued administration of such hormones will continue to initiate new sites of resorption the use of such hormones alone will not always bring about the desired increase in total bone.

Since it now appears that 24-epi-1,25-dihydroxyvitamin D$_2$ supports bone formation and mineralization but does not initiate new sites of resorption, a pulsed dosage regimen utilizing that 24-epi compound in combination with other vitamin D compounds or other homrones would seem to offer a significantly new approach to building bone mass. Such regimen would comprise initially administering a hormone, e.g. the hormonal forms of vitamin D, other hormones, or any of the vitamin D compounds which will induce bone mobilization, for a time sufficient to induce new bone resorption cavities, after which the hormone or vitamin D compound of choice is withdrawn from administration and 24-epi-1,25-dihydroxy vitamin D$_2$ is administered until net bone formation is realized. As an example of such regimen, the vitamin D compound or hormone can be administered on a daily basis for a period of one week or longer to initiate new bone resorption sites (Pulse 1) after which the compound or hormone of choice is withdrawn and 24-epi-1,25-dihydroxy-vitamin D$_2$ is administered for a period of from about two to about four months (Pulse 2). The 24-epi compound will thus support the formation of bone in the resorption sites initiated by the first step of the treatment regimen but will not initiate new resorption sites with the result that through this pulse regimen the desired net bone formation can be achieved.

Dosage forms of the various compounds can be prepared by combining them with non-toxic pharmaceutically acceptable carriers as is well known in the art. Such carriers may be either solid or liquid such as, for example, corn starch, lactose, sucrose, peanut oil, olive oil, sesame oil and propylene glycol. If a solid carrier is used the dosage form of the compounds may be tablets, capsules, powders, troches or lozenges. If a liquid carrier is used, soft gelatin capsules, or syrup or liquid suspensions, emulsions or solutions may be the dosage form. The dosage forms may also contain adjuvants, such as preserving, stabilizing, wetting or emulsifying agents, solution promoters, etc. They may also contain other therapeutically valuable substances.

24-epi-1,25-(OH)$_2$D$_2$ can be prepared in accordance with the following procedure and process scheme.

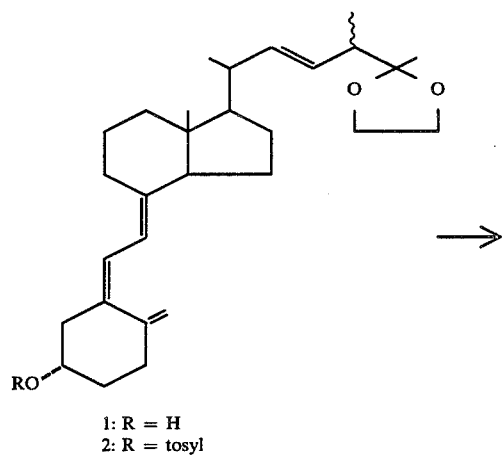

1: R = H
2: R = tosyl

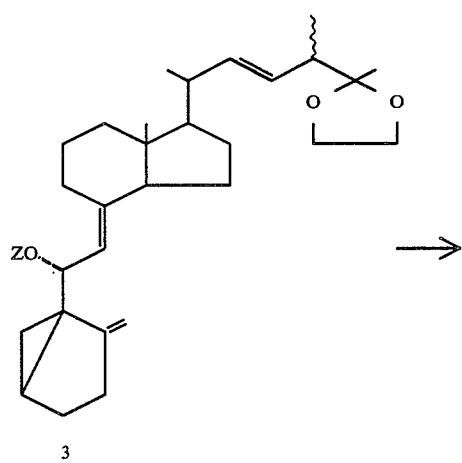

3

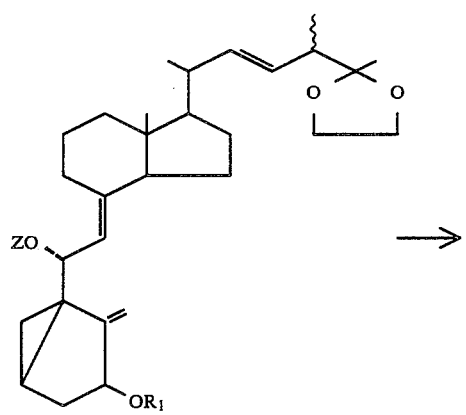

4: R₁ = H
5: R₁ = Acyl

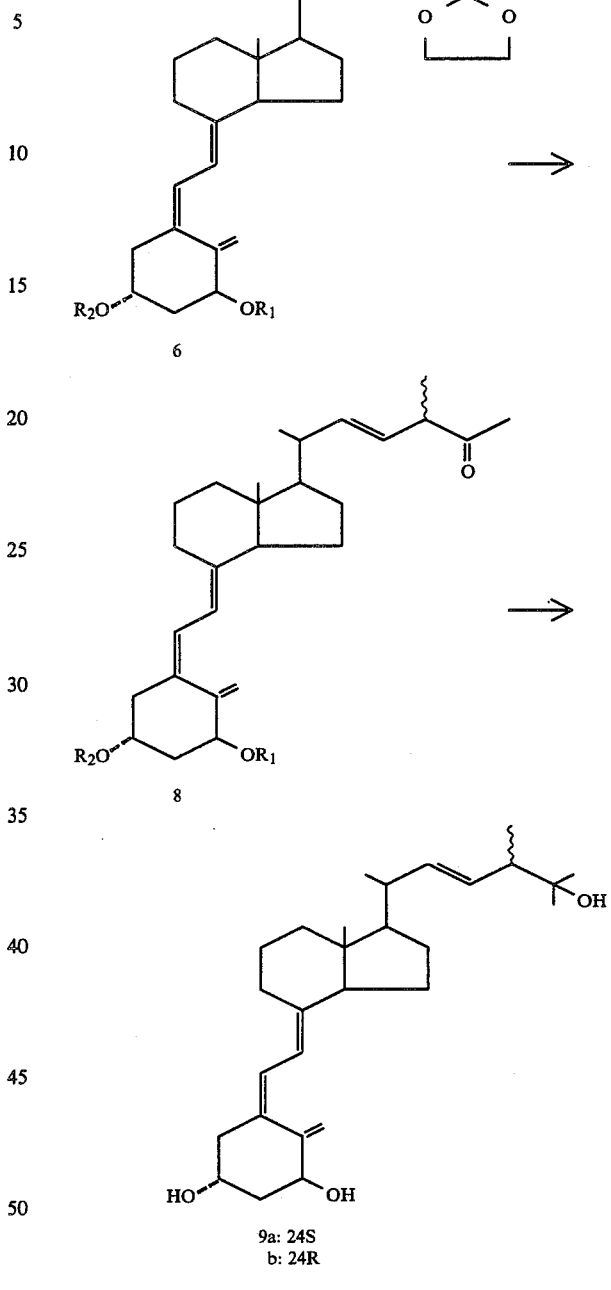

6

8

9a: 24S
b: 24R

1α-hydroxy-3,5-cyclovitamin D (4, Z=methyl)

A solution of compound (1) (50 mg) (as a mixture of the 24 R and S epimers) prepared in accordance with the procedures of U.S. Pat. No. 4,448,721 in dry pyridine (300 ul) is treated with 50 mg of p-toluenesulfonyl chloride at 4° C. for 30 h. The mixture is poured over ice/sat. NaHCO₃ with stirring and the product is extracted with benzene. The combined organic phases are washed with aqueous NaHCO₃, H₂O, aqueous CuSO₄ and water, dried over MgSO₄ and evaporated.

The crude 3-tosyl derivative (2) is directly solvolyzed in anhydrous methanol (10 ml) and NaHCO₃ (150 mg) by heating at 55° C. for 8.5 h with stirring. The reaction mixture is then cooled to room temperature and concentrated to 2 ml under vacuo. Benzene (80 ml) is then added and organic layer is washed with water, dried and evaporated. The resulting cyclovitamin (3, Z=methyl) can be used in the subsequent oxidation without further purification.

The crude product (3) in $CH_2Cl_2$ (4.5 ml) is added to an ice-cooled solution at $SeO_2$ (5.05 mg) and t-BuOOH (16.5 ul) in $CH_2Cl_2$ (8 ml) containing anhydrous pyridine (50 ul). After being stirred for 15 min at 0° C., the reaction mixture is allowed to warm to room temperature. After an additional 30 min, the mixture is transferred to a separatory funnel and shaken with 10% NaOH (30 ml). Ether (150 ml) is added and the separated organic phase is washed with 10% NaOH, water, dried and evaporated. The oily residue is purified on silica gel thin layer plates (20×20 cm plates, AcOEt/hexane 4:6) to yield 20 mg of 1α-hydroxy derivative (4, Z=methyl): mass spectrum, m/e: 470 (M+, 5), 438 (20), 87 (100); NMR ($CDCl_3$) δ0.53 (3H, s, 18-$H_3$), 0.63 (1H, m, 3-H), 4.19 (1H, d, J=9.5 Hz, 6-H), 4.2 (1H, m, 1-H) 4.95 (1H, d, J=9.5 Hz, 7-H), 5.17 and 5.25 (2H, each m, 19-$H_2$), 5.35 (2H, m, 22-H and 23-H).

Acetylation of compound (4)

A solution of cyclovitamin (4, Z=methyl) (18 mg) in pyridine (1 ml) and acetic anhydride (0.33 ml) is heated at 55° C. for 2 h. The mixture is poured into ice-cooled sat. $NaHCO_3$ and extracted with benzene and ether. The combined organic extracts are washed with water, saturated $CuSO_4$ and aqueous $NaHCO_3$ solutions, dried and evaporated to give 1-acetoxy derivative (5, Z=methyl, acyl=acetyl) (19 mg): mass spectrum, m/e: 512 (M+, 5), 420 (5), 87 (100); NMR ($CDCl_3$) δ0.53 (3H, s, 18-$H_3$), 4.18 (1H, d, J=9.5 Hz, 6-H), 4.97 (2H, m, 7-H and 19-H), 5.24 (2H, m, 1-H and 19-H), 5.35 (2H, m, 22-H and 23-H).

Solvolysis of 1α-acetoxy-3,5-cyclovitamin (5) ($R_1$=acetyl)

A solution of cyclovitamin (5) (4.5 mg) in 3:1 mixture of dioxane/$H_2O$ (1.5 ml) is heated at 55° C. p-Toluenesulfonic acid (1 mg in 20 l of $H_2O$) is then added and heating is continued for 15 min. The mixture is poured into saturated $NaHCO_3$/ice, and extracted with benzene and ether. The organic phases are washed with $NaHCO_3$ and water and dried over $MgSO_4$. Evaporation of solvents gives a residue containing compounds (6) (where $R_1$=acetyl and $R_2$=H) and (7) (where $R_1$=acetyl and $R_2$=H) which are separated by chromatography on HPLC (6.2 mm×25 cm Zorbax-Sil) using 2% of 2-propanol in hexane as an eluent. If necessary, the products are further purified by rechromatography.

Ketal hydrolysis in compound (6) to obtain ketone (8)

To the solution of ketal (6, $R_1$=acetyl, $R_2$=H) (1.35 mg) in ethanol (1.5 ml), p-toluenesulfonic acid (0.34 mg in 45 uL of $H_2O$) is added and the mixture is heated under reflux for 30 min. The reaction mixture is poured into diluted $NaHCO_3$, and extracted with benzene and ether. The combined organic extracts are washed with water, dried over $MgSO_4$ and evaporated. High-pressure liquid chromatography on the crude mixture (4% 2-propanol/hexane, 6.2 mm×25 cm Zorbax-Sil) affords some unreacted ketal (6) (0.12 mg, collected at 48 ml) and desired ketone (8, $R_1$=acetyl, $R_2$=H) (0.36 mg, collected at 52 ml), characterized by the following data: mass spectrum, m/e: 454 (M+, 9), 394 (17), 376 (10), 134 (23), 43 (100); NMR ($CDCl_3$) δ0.53 (3H, s, 18-$H_3$), 1.03 (3H, d, J=6.5 Hz, 21-$H_3$), 1.13 (3H, d, J=7.0 Hz, 28-$H_3$), 2.03 (3H, s, $CH_3COO$), 2.12 (3H, s, $CH_3CO$), 4.19 (1H, m, 3-H), 5.03 (1H, m, 19-H), 5.33 (3H, broad m, 19-H, 22-H and 23-H), 5.49 (1H, m, 1-H), 5.93 (1H, d, J=11 Hz, 7-H), 6.37 (1H, d, J=11 Hz, 6-H); UV (EtOH)$\lambda_{max}$ 266 nm, 250 nm, $\lambda_{min}$ 225 nm.

Reaction of ketone (8) with methylmagnesium bromide to obtain products (9a) and (9b)

Ketone (8, $R_1$=acetyl, $R_2$=H) in anhydrous ether is treated with the excess of $CH_3MgBr$ (2.85M solution in ether). The reaction mixture is stirred at room temperature for 30 min, then quenched with aq. $NH_4Cl$, extracted with benzene, ether and $CH_2Cl_2$. The organic phases are washed with dilute $NaHCO_3$, dried over $MgSO_4$ and evaporated. The mixture of (9a) and (9b) thus obtained is separated by high performance liquid chromatograhy (6% 2-propanol/hexane, 4.6 mm×25 cm Zorbax-Sil), to obtain, in order of elution, pure epimers (9a) and (9b). 1α,25-dihydroxyvitamin $D_2$ (9a): UV (EtOH)$\lambda_{max}$ 265.5 nm, $\lambda_{min}$ 227.5 nm; mass spectrum, m/e 428 (M+, 6), 410 (4), 352 (4), 287 (6), 269 (10), 251 (10), 152 (42), 134 (100), 59 (99); NMR ($CDCl_3$) δ0.56 (3H, s, 18-$H_3$), 1.01 (3H, d, J=6.5 Hz, 28-$H_3$), 1.04 (3H, d, J=6.5 Hz, 21-$H_3$), 1.14 and 1.18 (6H, each s, 26-$H_3$ and 27-$H_3$), 4.24 (1H, m, 3-H), 4.43 (1H, m, 1-H), 5.01 (1H, m, 19-H), 5.34 (3H, broad m, 19-H, 22-H and 23-H), 6.02 (1H, d, J=11 Hz, 7-H), 6.39 (1H, d, J=11 Hz, 6-H).

1α,25-dihydroxy-24-epivitamin $D_2$ (9b): UV (EtOH)-$\lambda_{max}$ 265.5 nm, $\lambda_{min}$ 227.5 nm; mass spectrum, m/e 428 (M+, 13), 410 (9), 352 (7), 287 (11), 269 (15), 251 (13), 152 (52), 134 (100), 59 (97).

We claim:

1. A method for preventing or treating physiological disorders in mammals, which disorders are characterized by a requirement to regenerate or prevent loss of bone mass, which comprises administering to said mammals an amount of 1 alpha,25-dihydroxy-24-epi vitamin $D_2$ sufficient to induce mineralization of bone and thereby to increase or prevent loss of net bone mass.

2. The method of claim 1 wherein the disorder is postmenopausal osteoporosis.

3. The method of claim 1 wherein the disorder is involutional osteoporosis.

4. The method of claim 1 wherein the disorder is senile osteoporosis.

5. The method of claim 1 wherein the disorder is steroid-induced osteoporosis.

6. The method of claim 2 wherein the compound is administered to women during and subsequent to menopause.

7. The method of claim 2 wherein the compound is administered to women prior to the onset of menopause.

8. The method of claim 1 wherein the compound is administered in an amount from about 0.5 microgram to about 25 micrograms per day.

9. The method of claim 1 wherein the compound, in solution in a liquid vehicle ingestible by and nontoxic to said mammals is administered orally in encapsulated form.

10. The method of claim 1 wherein 1α,25-dihydroxy-24-epi vitamin $D_2$ is administered in combination with at least one hormone or vitamin D compound characterized by the ability to mobilize bone in vivo.

11. The method of claim 10 where the bone mobilization-inducing compound is selected from parathyroid hormone vitamin $D_3$, vitamin $D_2$ 1α-hydroxyvitamin $D_3$, 1α-hydroxyvitamin $D_2$, 1α,25-dihydroxyvitamin $D_3$, 1α,25-dihydroxyvitamin $D_2$, 25-hydroxyvitamin $D_3$, 25-hydroxyvitamin $D_2$, 24-24-difluoro-25-hydroxyvitamin $D_3$, 24,24-difluoro-1α,25-dihydroxyvitamin $D_3$, 24-fluoro-25-hydroxyvitamin $D_3$, 24-fluoro-1α,25-dihydroxyvitamin $D_3$, 2β-fluoro-25-hydroxyvitamin $D_3$, 2β-fluoro-1α-hydroxyvitamin $D_3$, 2β-fluoro-1α,25-dihydroxyvitamin $D_3$, 26,26,26,27,27,27-hexafluoro-25-hydroxyvitamin $D_3$, 26,26,26,27,27,27-hexafluoro-1α,25-dihydroxyvitamin $D_3$, 24,25-dihydroxyvitamin $D_3$, 1α,24,25-trihydroxyvitamin $D_3$, 25,26-dihydroxyvitamin $D_3$, 1α,25,26-trihyroxyvitamin $D_3$.

12. The method of claim 10 wherein the administration is the pulse regimen comprising initially administering a hormone or vitamin D compound characterized by its ability to mobilize bone in vivo for a time sufficient to induce new bone resorption cavities, then discontinuing such administration and commencing the administration of 24-epi-1α,25-dihydroxyvitamin $D_2$ until net bone formation has been realized.

13. The method of claim 11 wherein the administration is the pulse regimen.

14. The method of claim 13 wherein the vitamin D compound is 1α,25-dihydroxyvitamin $D_3$ or 1α,25-dihydroxyvitamin $D_2$.

15. The method of claim 13 wherein the hormone is parathyroid hormone.

16. A pharmaceutical composition comprising 1α,25-dihydroxy-24-epi vitamin $D_2$ and a pharmaceutically acceptable excipient.

17. A pharmaceutical composition comprising 1 alpha,25-dihydroxy-24-epi-vitamin $D_2$ and at least one bone mobilization inducing compound selected from the group consisting of the bone-mobilization inducing compounds set forth in claim 12.

18. The pharmaceutical composition of claim 17 wherein the bone mobilization-inducing compound is a vitamin D derivative selected from the group consisting of 25-hydroxyvitamin $D_3$, 25-hydroxyvitamin $D_2$, 1α-hydroxyvitamin $D_3$, 1α-hydroxyvitamin $D_2$, 1α,25-dihydroxyvitamin $D_3$, 1α,25-dihydroxyvitamin $D_2$, 24,24-difluoro-25-hydroxyvitamin $D_3$, 24,24-difluoro-1α,25-dihydroxyvitamin $D_3$, 24-fluoro-25-hydroxyvitamin $D_3$, 24-fluoro-1α,25-dihydroxyvitamin $D_3$, 26,26,26,27,27,27-hexafluoro-1α,25-dihydroxyvitamin $D_3$, 26,26,26,27,27,27-hexafluoro-25-hydroxyvitamin $D_3$, 2β-fluoro-1α-hydroxyvitamin $D_3$, 2β-fluoro-25-hydroxyvitamin $D_3$, 24,25-dihydroxyvitamin $d_3$, 1α,24,25-trihydroxyvitamin $D_3$, 25,26-dihydroxyvitamin $D_3$, 1α,25,26-trihydroxyvitamin $D_3$.

* * * * *